United States Patent [19]

Macaulay et al.

[11] Patent Number: 5,120,541
[45] Date of Patent: Jun. 9, 1992

[54] COSMETIC COMPOSITION

[75] Inventors: Ernest W. Macaulay, Bromborough; Sally E. Tansley, Frankby, both of England

[73] Assignee: Chesebrough-Pond'3 s USA Co., Division of Conopco, Inc., Greenwich, Conn.

[21] Appl. No.: 667,983

[22] Filed: Mar. 12, 1991

[30] Foreign Application Priority Data

Mar. 12, 1990 [GB] United Kingdom ............... 9005523

[51] Int. Cl.$^5$ ............................ A61K 6/00; A61K 7/42
[52] U.S. Cl. ...................................... 424/401; 424/59; 424/63; 424/64; 424/DIG. 5; 424/195.1
[58] Field of Search ..... 252/312 424/49, DIG. 5, 63, 424/64, 65, 401

[56] References Cited

U.S. PATENT DOCUMENTS

| | | | |
|---|---|---|---|
| 3,148,125 | 9/1964 | Strianse et al. | 424/DIG. 5 |
| 4,268,498 | 5/1981 | Gedeon et al. | 424/DIG. 5 |
| 4,504,465 | 3/1985 | Sampson et al. | 424/DIG. 5 |
| 4,617,185 | 10/1986 | DiPietro | 424/DIG. 5 |
| 4,948,578 | 8/1990 | Burger et al. | 424/66 |
| 4,988,453 | 1/1991 | Chambers et al. | 252/122 |
| 5,000,937 | 3/1991 | Grollier et al. | 424/DIG. 5 |

FOREIGN PATENT DOCUMENTS

| | | |
|---|---|---|
| 0089120 | 9/1983 | European Pat. Off. |
| 0107330 | 5/1984 | European Pat. Off. |
| 0284765 | 10/1988 | European Pat. Off. |

*Primary Examiner*—Thurman K. Page
*Assistant Examiner*—D. Colucci
*Attorney, Agent, or Firm*—Milton L. Honig

[57] ABSTRACT

A transparent cosmetic stick composition having a lamellar structure comprising:
(a) from 5 to 95% by weight of an alcohol,
(b) from 3 to 20% by weight of a soap,
(c) from 0.1 to 10% by weight of a soap crystal growth inhibitor, and
(d) from 0 to 30% by weight of water.

15 Claims, No Drawings

COSMETIC COMPOSITION

FIELD OF INVENTION

The invention relates to transparent cosmetic compositions, and particularly to transparent stick compositions. The invention is also concerned with a process for making these compositions.

BACKGROUND AND PRIOR ART

Conventionally, transparent cosmetic compositions have been made using a soap/alcohol formulation. Such compositions have been formed as gelled sticks which act as vehicles for delivery of active ingredients.

U.S. Pat. No. 4,268,498 (Revlon) describes clear cosmetic sticks comprising a soap/alcohol gel base. It mentions two problems associated with previous soap/alcohol formulations: that the sticks are initially clear but become hazy with time, and that evaporation of the alcohol causes shrinkage of the stick. It proposes the use of polyoxyethylene-glucose fatty acid esters and of ethers of long-chain alcohols to replace short-chain monohydric alcohols. However, desirable cosmetic features such as cooling effect are thereby lost.

In EP 107 330 (Procter & Gamble), there is disclosed a transparent soap gel stick composition which contains hydro-alcoholic soluble emollient. The composition contains less than 12.5% of a short chain monohydric alcohol, e.g. ethanol. However, there is not mention of the inclusion of a clarity-inducing component.

Transparent sticks can be prepared and manufactured by ensuring complete neutralisation of the fatty acids, but this requires an increase in the pH of the composition to unacceptably high levels, approximately pH 10.

Further neutralisation to pH 7 means that free fatty acid will be present which may form acid soap crystals providing nucleation sites leading to the growth of large soap crystals. This growth of large crystals destroys the transparency of the composition either immediately or on gradual cooling.

It has surprisingly been found that when certain compounds are included in the cosmetic composition, the growth of soap crystals in the composition is inhibited, and transparency is achieved even at high levels of monohydric alcohol. Furthermore, such compositions can, if desired, be formulated entirely from natural plant-derived materials, that is, materials obtained from microbial culture and/or from higher plants.

DEFINITION OF THE INVENTION

The invention provides a transparent cosmetic composition having a lamellar structure comprising:
(a) from 5 to 95% by weight of an alcohol;
(b) from 3 to 20% by weight of a soap;
(c) from 0.1 to 10% by weight of a soap crystal growth inhibitor; and
(d) from 0 to 30% by weight of water.

DISCLOSURE OF THE INVENTION

(A) The Alcohol

The composition according to the invention comprises an alcohol component which may be monohydric or polyhydric or combinations thereof. The alcohol component may comprise ethanol, isopropanol, preferably propylene glycol or butanediol, most preferably glycerol. The alcohol component is present in an amount from 5 to 95% by weight.

(B) The Soap

The composition according to the invention comprises a soap. Preferably the soap is a straight chain saturated unsubstituted soap with chain length at least $C_{16}$, for example a palmitate or a stearate, and especially it may comprise a mixture of palmitate and stearate, preferably with the ratio between palmitate and stearate being between 60:40 and 40:60. The soap is present in an amount from 3 to 10% by weight, and preferably in an amount from 5 to 10% by weight. The soap may be neutralised with alkali metal, alkaline earth, Group III metal ions (e.g. $Al\,3+$), alkanol ammonium or any other suitable cation. The soap chains form into layers, providing the stick with its lamellar structure.

(C) The Soap Crystal Growth Inhibitor

The composition according to the invention comprises a soap crystal growth inhibitor. It may be appreciated that any soap crystal growth inhibitor which renders transparent the composition of the invention will be suitable for use in such a composition. The soap crystal growth inhibitor is present in an amount from 0.1 to 10%, and preferably in an amount from 0.1 to 4% by weight of the composition. The growth inhibitor will be a molecule which is likely to be incorporated into the soap crystal lattice but will not be so compatible as to form an unmodified mixed crystal.

Examples of suitable crystal growth inhibitors are:
(a) monoglycerides, diglycerides, triglycerides of $C_6-C_{24}$ saturated or unsaturated, straight- or branched-chain fatty acids or substituted fatty acids;
(b) salts of substituted fatty acids, wherein the fatty acid may be saturated or unsaturated, straight or branched-chain, and wherein the salt may be formed by any suitable cation. The substituents may include hydroxy, thiol, substituted thiol, mono- and di-substituted amines, ethers, ketones and the like.
(c) salts of branched-chain fatty acids (saturated or unsaturated) formed with any suitable cation;
(d) short-chain (C3–C20) peptides;
(e) other suitable materials including substituted or unsubstituted short-chain nonionics ($<C_{24}$) derived from, e.g., alcohols, ethylene, propylene or butylene oxide, sorbitan esters, rosins, lanolin and similar compounds.

The above exemplified inhibitors may be used singly or in mixtures. Preferred crystal growth inhibitors include glyceryl monolaurate, sodium ricinoleate (a $C_{18}$ branched chain fatty acid) and sodium isostearate.

(D) Water

The composition according to the invention comprises from 0 to 30% by weight of water.

(E) Other Ingredients

In addition to the essential ingredients defined herein, there may also be included in the cosmetic composition of the invention other ingredients, provided they do not destroy the transparency of the composition. Examples of additives are emollients, perfumes, dyes, antimicrobial agents, deodorants, deoperfumes, sunscreens and skin modifiers, as well as other additives known in this field.

ADVANTAGES OF THE INVENTION

The transparent cosmetic composition of the invention may be formed as a solid transparent stick. In all cases, the addition of a soap crystal growth inhibitor to the soap/alcohol mixture allows transparency to be attained even at levels of monohydric alcohol of up to 95% by weight. A composition containing high levels of such alcohols confers a pleasant cooling effect on the skin and is non-sticky. By selection of suitable packaging, it is possible to avoid the problem of shrinkage due to evaporation of alcohol. The composition of the invention retains its transparency on storage.

PROCESS

The invention also provides a process for preparing a transparent cosmetic composition as herein defined. The process comprises combining the ingredients in liquid form. To manufacture a transparent stick, the combined ingredients are poured into a container having a particular shape so that the solid which forms takes the shape of the container.

EXAMPLES

A number of compositions were prepared according to the procedure described herein (all % by weight formulations).

Transparency was evaluated in two ways:
(a) the test given in U.S. Pat. No. 3,274,119 wherein "transparent" is defined as such that a bold face type of 14 point size can be readily read through a ¼ inch section of material;
(b) thin slices (approximately 5 mm) of the sticks were taken and viewed through a cross-polarising lens. This shows crystal facets. The less the number of facets, the more transparent the products. The "blacker" the cross-polarised image, the more transparent it is. Structures according to the present invention are noted to have 'maltese cross' images.

Formulations according to the invention which contained the soap crystal growth inhibitor were found to be more "transparent" than similar formulations which did not include the soap crystal growth inhibitor.

INGREDIENTS

| Example | Isopropanol | IMS (Alcohol) | Glycerol | $C_{16}C_{18}$ Fatty Acid | NaOH | Glyceryl Monolaurate | Sodium salt of Ricinoleic Acid | Perfume | Water | Propylene Glycol |
| --- | --- | --- | --- | --- | --- | --- | --- | --- | --- | --- |
| 1 | — | 65.0 | 25.6 | 6.4 | 1.0 | 1.0 | — | 1.0 | — | — |
| 2 | — | 25.0 | 58.1 | 6.4 | 1.0 | 1.0 | — | 1.0 | 7.5 | — |
| 3 | — | 35.0 | 50.6 | 6.4 | 1.0 | 1.0 | — | 1.0 | 5.0 | — |
| 4 | — | 63.0 | 25.6 | 6.4 | 1.0 | 1.0 | — | 1.0 | 2.0 | — |
| 5 | — | 46.0 | 43.9 | 7.0 | 1.1 | 1.0 | — | 1.0 | — | — |
| 6 | — | 25.5 | — | 6.0 | 0.9 | — | 1.0 | 1.0 | 5.6 | 60.0 |
| 7 | — | 20.0 | — | 7.0 | 1.0 | — | 1.0 | 1.0 | — | 70.0 |
| 8 | — | 25.0 | 15.0 | 7.0 | 1.0 | — | 1.0 | 1.0 | 4.5 | 45.5 |
| 9 | 35.0 | 30.0 | 25.6 | 6.4 | 1.0 | 1.0 | — | 1.0 | — | — |
| 10 | 33.0 | 30.0 | 25.6 | 6.4 | 1.0 | 1.0 | — | 1.0 | 2.0 | — |

(All figures are weight proportions of the total composition)

If sticks containing very low levels of water are to be made, sodium hydroxide may be added to the alcohol and the solution heated with constant stirring to reflux. When completely dissolved all the remaining ingredients except the perfume, anti-bacterial agent and the like minor ingredients may be added, the solution stirred and once more heated to reflux. Finally, the solution is cooled to about 60° C., minor ingredients such as perfume added to the homogenous solution and the sticks cast into appropriate barrels.

PRODUCT FORMS AND PACKAGING

A preferred embodiment of the invention is in the form of a stick of circular or oval cross-section contained in a stick dispenser. Suitable dispensers have an airtight cap so as to prevent evaporation of volatile ingredients during storage between uses. The composition of the invention can also be dispensed as a cream or soft gel from an applicator suitable for the purpose.

USE OF THE INVENTION

The transparent cosmetic composition of the invention is applied to areas of the skin as desired. In the case of a transparent stick, the stick is rubbed on the skin so as to leave a deposit of the cosmetic composition. By this means, additives which are included in the cosmetic composition may be spread onto the skin in the quantities required.

We claim:

1. A transparent cosmetic stick composition having a lamellar structure comprising:
   (a) from 20 to 65% by weight of a monohydric alcohol;
   (b) from 25.6 to 70% by weight of a polyhydric alcohol;
   (c) from 0.1 to 10% by weight of a soap crystal growth inhibitor selected from the group consisting of glycerol monolaurate, sodium ricinoleate and sodium isostearate;
   (d) from 3 to 20% by weight of a soap; and
   (e) from 0 to 30% by weight of water.

2. A cosmetic composition as claimed in claim 1, wherein the monohydric alcohol component is selected from the group consisting of ethanol, isopropanol and mixtures thereof.

3. A cosmetic composition as claimed in claim 1, wherein the polyhydric alcohol component is selected from the group consisting of glycerol, propylene glycol, butane diol or mixtures thereof.

4. A cosmetic composition as claimed in claim 1, wherein the soap comprises a palmitate.

5. A cosmetic composition as claimed in claim 1, wherein the soap comprises a stearate.

6. A cosmetic composition as claimed in claim 1, wherein the soap comprises a mixture of a palmitate and a stearate.

7. A cosmetic composition as claimed in claim 6, wherein the ratio of stearate to palmitate is in the range 40:60 to 60:40.

8. A cosmetic composition as claimed in claim 6, wherein the soap is present in an amount from 5 to 10% by weight.

9. A cosmetic composition as claimed in claim 1, wherein the crystal growth inhibitor is glyceryl monolaurate.

10. A cosmetic composition as claimed in claim 1, wherein the crystal growth inhibitor is sodium ricinoleate.

11. A cosmetic composition as claimed in claim 1, wherein the crystal growth inhibitor is sodium isostearate.

12. A cosmetic composition as claimed in claim 1 wherein the soap crystal growth inhibitor is present in an amount from 0.1 to 4% by weight of the composition.

13. A cosmetic composition as claimed in claim 1, wherein the ingredients are natural plant derived materials.

14. A process for preparing a transparent cosmetic composition as claimed in claim 1, comprising combining the ingredients (a) through (e) in liquid form.

15. A process for preparing a transparent stick composition as claimed in claim 14, comprising combining the ingredients in liquid form and pouring them into a container having a particular shape so that the solid which forms takes the shape of the container.

* * * * *

UNITED STATES PATENT AND TRADEMARK OFFICE
CERTIFICATE OF CORRECTION

PATENT NO. : 5,120,541

DATED : June 9, 1992

INVENTOR(S) : Ernest W. Macaulay; Sally E. Tansley

It is certified that error appears in the above-identified patent and that said Letters Patent is hereby corrected as shown below:

On the title page: Item [73] Assignee should read:

--Chesebrough-Pond's USA Co., Division of Conopco, Inc.--.

Signed and Sealed this

Tenth Day of August, 1993

Attest:

MICHAEL K. KIRK

Attesting Officer     Acting Commissioner of Patents and Trademarks